US00PP34995P2

(12) United States Plant Patent
Goff

(10) Patent No.: US PP34,995 P2
(45) Date of Patent: Feb. 21, 2023

(54) ***HEMEROCALLIS* PLANT NAMED 'DLPG17947'**

(50) Latin Name: *Hemerocallis hybrida*
Varietal Denomination: DLPG17947

(71) Applicant: Gregory B. Goff, Micanopy, FL (US)

(72) Inventor: Gregory B. Goff, Micanopy, FL (US)

( * ) Notice: Subject to any disclaimer, the term of this patent is extended or adjusted under 35 U.S.C. 154(b) by 0 days.

(21) Appl. No.: 17/895,455

(22) Filed: Aug. 25, 2022

Related U.S. Application Data

(60) Provisional application No. 63/255,313, filed on Oct. 13, 2021.

(51) Int. Cl.
*A01H 5/02* (2018.01)
*A01H 6/56* (2018.01)

(52) U.S. Cl.
USPC ..... Plt./312

(58) Field of Classification Search
USPC ..... Plt./263.1, 312
See application file for complete search history.

(56) References Cited

U.S. PATENT DOCUMENTS

PP26,329 P3 * 1/2016 Westmoreland ..... A01H 6/00
Plt./312

* cited by examiner

*Primary Examiner* — Karen M Redden
(74) *Attorney, Agent, or Firm* — C. Anne Whealy

(57) ABSTRACT

A new and distinct cultivar of *Hemerocallis* plant named 'DLPG17947', characterized by its relatively compact and upright plant habit; vigorous growth habit; medium green-colored leaves that are outwardly arching; early, freely and remontant flowering habit throughout the and summer; relatively large bright yellow-colored flowers that face outwardly and are not persistent; food garden performance; and resistance to Daylily Rust.

2 Drawing Sheets

Figure 1:
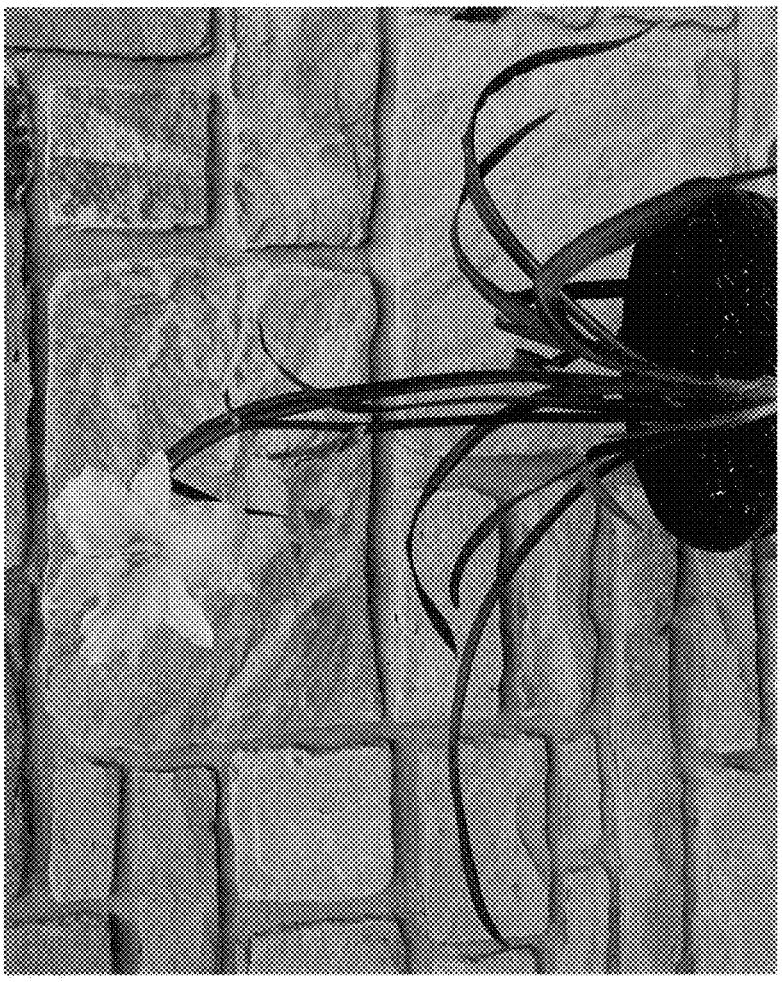

Botanical designation: *Hemerocallis hybrida.*
Cultivar denomination: 'DLPG17947'.

BACKGROUND OF THE INVENTION

The present Invention relates to a new and distinct cultivar of *Hemerocallis* plant, commercially referred to as Daylily, botanically known as *Hemerocallis hybrida* and hereinafter referred to by the name 'DLPG17947'.

The new *Hemerocallis* plant is a product of a planned breeding program conducted by the Inventor in Micanopy, Fla. The objective of the breeding program is to develop new compact and early flowering *Hemerocallis* plants with numerous attractive flowers, disease resistance and good garden performance.

The new *Hemerocallis* plant originated from an open-pollination in May, 2016 of a proprietary selection of *Hemerocallis hybrida* identified as code number 6901, not patented, with an unknown proprietary selection of *Hemerocallis hybrida* as the male, or pollen, parent. The new *Hemerocallis* plant was discovered and selected by the Inventor as a single flowering plant from within the resultant progeny of the stated open-pollination in a controlled environment in Micanopy, Fla. in April, 2017.

Asexual reproduction of the new *Hemerocallis* plant by divisions in a controlled environment in Micanopy, Fla. and Elburn, Ill. since October, 2017 has shown that the unique features of this new *Hemerocallis* plant are stable and reproduced true to type in successive generations.

SUMMARY OF THE INVENTION

Plants of the new *Hemerocallis* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'DLPG17947'. These characteristics in combination distinguish 'DLPG17947' as a new and distinct *Hemerocallis* plant:

1. Relatively compact and upright plant habit.
2. Vigorous growth habit.
3. Medium green-colored leaves that are outwardly arching.
4. Early, freely and remontant flowering habit throughout the summer.
5. Relatively large bright yellow-colored flowers that face outwardly and are not persistent.
6. Good garden performance.
7. Resistant to Daylily Rust.

Plants of the new *Hemerocallis* differ primarily from plants of the female parent selection in the following characteristics:

1. Plants of the new *Hemerocallis* are more compact than plants of the female parent selection.
2. Plants of the new *Hemerocallis* divide more readily than plants of the female parent selection.
3. Plants of the new *Hemerocallis* have larger flowers than plants of the female parent selection.
4. Plants of the new *Hemerocallis* are more freely flowering than plants of the female parent selection.
5. Plants of the new *Hemerocallis* flower more remontantly than plants of the female parent selection.

6. Plants of the new *Hemerocallis* will flower at lower temperatures than plants of the female parent selection.

Plants of the new *Hemerocallis* can be compared to plants of the *Hemerocallis hybrida* 'Stella d'Oro', not patented. Plants of the new *Hemerocallis* differ from plants of 'Stella d'Oro' in the following characteristics:

1. Plants of the new *Hemerocallis* are more freely flowering than plants of 'Stella d'Oro'.
2. Plants of the new *Hemerocallis* have larger flowers than plants of 'Stella d'Oro'.
3. Plants of the new *Hemerocallis* tolerate low and high temperatures better than plants of 'Stella d'Oro'.
4. Plants of the new *Hemerocallis* are resistant to Daylily Rust whereas plants of 'Stella d'Oro' are susceptible to Daylily Rust.

DESCRIPTION OF THE PHOTOGRAPHS

The accompanying colored photographs illustrate the overall appearance of the new *Hemerocallis* plant showing the colors as true as it is reasonably possible to obtain in colored reproductions of this type. Colors in the photographs may differ slightly from the color values cited in the detailed botanical description which accurately describe the colors of the new *Hemerocallis* plant.

The photograph on the first sheet (FIG. 1) comprises a side perspective view of a typical flowering plant of 'DLPG17947' grown in container.

Figure 2:
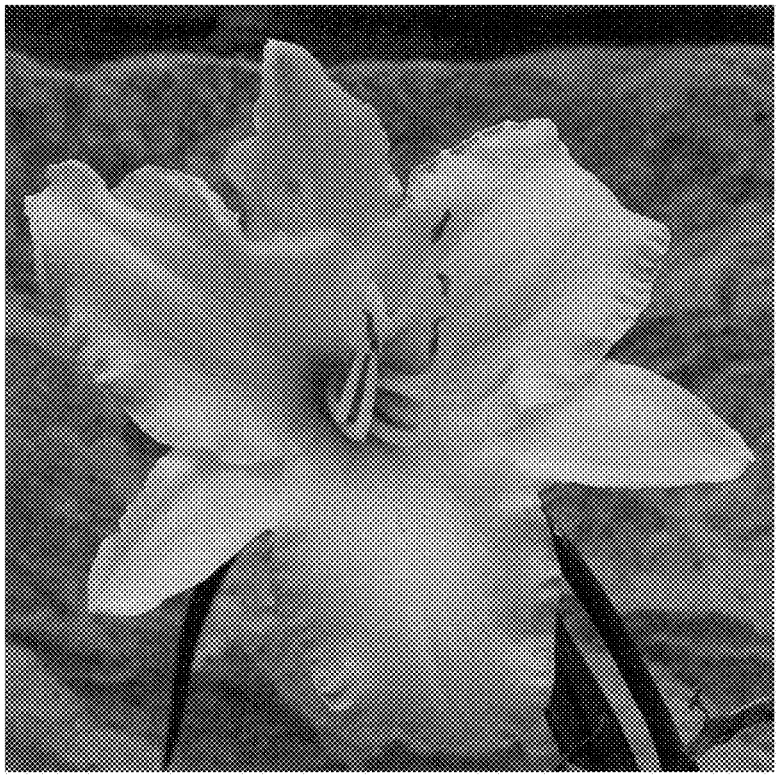

The photograph on the second sheet (FIG. 2) is a close-up view of a typical flower of 'DLPG17947'.

DETAILED BOTANICAL DESCRIPTION

The aforementioned photographs and following observations and measurements describe plants grown during the summer in 1.5-gallon containers in an outdoor nursery in West Chicago, Ill. and under cultural practices typically used in commercial *Hemerocallis* production. During the production of the plants, day temperatures averaged 24° C. and night temperatures averaged 18° C. Plants were 18 months old when the photographs and description were taken. In the following description, color references are made to The Royal Horticultural Society Colour Chart, 2015 Edition, except where general terms of ordinary dictionary significance are used.

Botanical classification: *Hemerocallis hybrida* 'DLPG17947'.

Parentage:

*Female, or seed, parent*.—Proprietary selection of *Hemerocallis hybrida* identified as code number 6901, not patented.

*Male, or pollen, parent*.—Unknown proprietary selection of *Hemerocallis hybrida*, not patented.

Propagation:

*Type*.—By divisions.

*Root description*.—Thick, fleshy; typically tan to golden brown in color, actual color of the roots is dependent on substrate composition, water quality, fertilizers, substrate temperature and physiological age of roots.

*Rooting habit*.—Moderately freely branching, dense.

Plant Description:

*Plant and growth habit*.—Upright plant habit; erect flowering stems with a terminal cluster of flowers arising from the leaf axils; relatively compact and dense plant habit; vigorous growth habit.

*Plant height, soil level to top of foliar plane*.—About 34 cm.

*Plant height, soil level to top of floral plane*.—About 52 cm.

*Plant diameter or spread*.—About 55 cm.

*Leaves*.—Arrangement: Alternate, simple; sessile. Length: About 48.5 cm. Width: About 2.8 cm. Shape: Linear. Apex: Long acute. Base: Clasping. Margin: Entire with broad undulations. Aspect: Carinate; initially upright to outwardly arching and occasionally twisting with development. Texture and luster, upper surface: Smooth, glabrous; moderately glossy. Texture and luster, lower surface: Smooth, glabrous; matte. Venation pattern: Parallel. Color: Developing leaves, upper and lower surfaces: Close to 144A; at the base, close to NN155C to NN155D; venation, close to 144A. Fully expanded leaves, upper and lower surface: Close to 146A; at the base, close to NN155C to NN155D; venation, close to 146A.

Flower description:

*Flower shape and aspect*.—Flowers umbellate and trumpet-shaped; when fully opened, inner tepals moderately recurved; flowers face mostly outwardly.

*Flowering habit*.—Freely flowering habit, large bulbs may produce up to 30 flowers per flowering stem.

*Fragrance*.—Slightly fragrant; sweet, pleasant.

*Natural flowering season*.—Plants flower throughout the summer in Northern Illinois.

*Postproduction longevity*.—Depending on temperature, flowers last about one to two days on the plant; not persistent.

*Flower buds, when tepals are starting to separate*.—Length: About 5.5 cm. Diameter: About 2 cm. Shape: Narrowly oblong. Color: Close to 13B.

*Flower size, not including reproductive organs*.—Diameter: About 11.5 cm by 12 cm. Length (height): About 6 cm. Throat diameter: About 5 mm. Tube length: About 3.2 cm. Tube diameter: About 7.5 mm.

*Perianth*.—Quantity and arrangement: Six tepals per flower arranged in two whorls; inner tepals imbricate and outer tepals not imbricate. Tepal length, inner tepals: About 6.7 cm to 7.2 cm. Tepal width, inner tepals: About 4.3 cm to 4.5 cm. Tepal length, outer tepals: About 6.6 cm to 7 cm. Tepal width, outer tepals: About 2.3 cm to 2.5 cm. Tepal shape, inner tepals: Obovate. Tepal shape, outer tepals: Lanceolate. Tepal apex, inner tepals: Obtuse. Tepal apex, outer tepals: Acute. Tepal margin, inner tepals: Mostly entire to shallowly crenate; ruffled. Tepal margin, outer tepals: Mostly entire; ruffled. Tepal texture, upper and lower surfaces, inner and outer tepals: Smooth, glabrous; velvety; matte. Tepal color, inner tepals: When opening and fully opened, upper surface: Close to between 13A and 14A; color does not change with subsequent development. When opening and fully opened, lower surface: Close to 13A to 13B; color does not change with subsequent development. Tepal color, outer tepals: When opening and fully opened, upper surface: Close to between 13A and 14A; towards the base, slightly tinged with close to 144A; color does not change with subsequent development. When opening and fully opened, lower surface: Close to 13B; towards the base, slightly tinged with close to 144A; color does not change with subsequent development.

Throat: Close to 10A. Tube: Close to 10B slightly tinged with close to 144A.

*Scapes*.—Length: About 41 cm. Diameter: About 7 mm by 8 mm. Strength: Strong, firm. Aspect: Erect. Texture and luster: Smooth, glabrous; slightly glaucous. Color: Close to between 146A and 147A.

*Scape leaves*.—Arrangement: One below each floral cluster and occasionally one along the length of the scape. Length: About 4.9 cm. Width: About 2.1 cm. Shape: Narrowly deltoid. Texture and luster, upper and lower surfaces: Smooth, glabrous; slightly glossy. Color, upper surface: Close to 144A. Color, lower surface: Close to 146A.

*Pedicels*.—Length: About 1 cm. Diameter: About 3 mm. Angle: About 30° to 45° from scape axis. Strength: Strong, firm. Texture: Smooth, glabrous; slightly glaucous. Color: Close to 146A.

*Reproductive organs*.—Stamens: Quantity per flower: Six. Filament length: About 5 cm. Filament color: Close to 17A. Anther size: About 7 mm by 1.5 mm. Anther color: Close to 23A. Pollen amount: Scarce. Pollen color: Close to 23A. Pistils: Quantity per flower: One. Style length: About 9 cm. Style color: Close to 17A. Ovary color: Close to 144A.

*Fruits and seeds*.—To date, fruit and seed development have not been observed on plants of the new *Hemerocallis*.

Pathogen & pest resistance: Plants of the new *Hemerocallis* have been observed to be resistant to Daylily Rust (*Puccinia hemerocallidis*). To date, plants of the new *Hemerocallis* have not been observed to be resistant to pests and other pathogens common on plants of *Hemerocallis*.

Garden performance: Plants of the new *Hemerocallis* have exhibited good tolerance to drought, flood, wind and have been observed to be suitable for USDA Hardiness Zones 3 to 12.

It is claimed:

1. A new and distinct *Hemerocallis* plant named 'DLPG17947' as illustrated and described.

* * * * *